United States Patent [19]

Nakos et al.

[11] Patent Number: 5,386,047
[45] Date of Patent: Jan. 31, 1995

[54] DI-α-CYANOPENTADIENOATE DISILOXANE COMPOUNDS FOR USE IN ADHESIVES

[75] Inventors: Steven T. Nakos, Andover; John G. Woods, Farmington, both of Conn.

[73] Assignee: Loctite Corporation, Hartford, Conn.

[21] Appl. No.: 209,785

[22] Filed: Mar. 11, 1994

[51] Int. Cl.⁶ .......................... C07F 7/10; C08F 30/08
[52] U.S. Cl. ........................... 556/416; 556/401; 526/279
[58] Field of Search ............... 556/416, 401; 526/279

[56] References Cited

U.S. PATENT DOCUMENTS

| | | | |
|---|---|---|---|
| 3,142,698 | 7/1964 | Halpern et al. | 260/465.4 |
| 3,316,227 | 4/1967 | Gerber | 260/88.7 |
| 3,554,990 | 1/1971 | Quinn | 260/88.7 |
| 4,012,402 | 3/1977 | Buck | 556/416 |
| 4,153,641 | 5/1979 | Deichert et al. | 260/827 |
| 4,276,402 | 6/1981 | Chromecek et al. | 556/416 X |
| 4,313,865 | 2/1982 | Teramoto et al. | 260/31.4 |
| 4,425,471 | 1/1984 | Millet | 526/29.8 |
| 4,793,886 | 12/1988 | Okamura et al. | 156/307.3 |
| 4,810,766 | 3/1989 | Ohmori et al. | 526/279 |
| 4,965,387 | 10/1990 | Shinohara et al. | 556/440 |
| 5,136,065 | 8/1992 | Yeh | 556/415 |
| 5,140,084 | 8/1992 | Mikuni et al. | 527/279 |
| 5,187,048 | 2/1993 | Woods et al. | 430/286 |
| 5,194,460 | 3/1993 | Evans et al. | 523/211 |
| 5,200,238 | 4/1993 | McArdle et al. | 428/1 |

FOREIGN PATENT DOCUMENTS

| | | |
|---|---|---|
| 49-2009 | 1/1974 | Japan . |
| 56-135570 | 10/1981 | Japan . |
| 56-135571 | 10/1981 | Japan . |

(List continued on next page.)

OTHER PUBLICATIONS

Gerber, *J. Polym. Prepr.*, 9, 434 (1968).
Trofimov et al., *Zh. Vses. Kim. O-va.*, 19, 473-4 (1974).
Aronovich, Trofimov et al., *Osnovn. Organ. Stintez i Neftekhmiya*, 8 50-53 (1977). (Abstract).
Denchev et al., *J. Applied Polymer Science*, 42, 2933-2941 (1991).
Denchev et al., *J. Applied Polymer Science*, 47, 1019-1026 (1993).
Vijayalakshmi et al., *J. Applied Polymer Science*, 49, 1387-1394 (1993).
Kadykov, et al, *Plast. Massy*, 1984, No. 10, pp. 8-9 (translation).
Sasaki et al, *J. Chem. Soc.*, C, 1, 196-200 (1971) (Abstract).
Kotsev. D., et al *Angew, Makromol, Chem.*, 92 41-52 (1980) (Abstract).
Kotsev. D., et al, *Izu. Khim.*, 14, 288-94 (1982) (Abstract).
Vijayalakshmi, V., et al *J. Adhes. Sci. Technol.* 4 733-50 (1990) (Abstract).
Birch, et al, *J. Chem. Soc.*, 1923, 244B.
Rao, et al, *Tetrahedron Lett.*, 32, 5821-5822 (1991).

*Primary Examiner*—Paul F. Shaver
*Attorney, Agent, or Firm*—Vidas, Arrett & Steinkraus

[57] ABSTRACT

Anionically polymerizable di-α-cyanopentadienoate disiloxane compounds of the formula:

$$[CH_2=CH-CH=C(CN)-C(=O)-O-CH_2-R-Si(R'')_2]_2-O$$

where R is $-CH=CH-$ or $-C(=CH_2)-$ and the R'' groups are the same or different hydrocarbon or halo substituted hydrocarbon groups are prepared by hydrolysis of a cyanoacetoxypropenylsilane having a hydrolyzable group attached to the silicon atom and then condensing the resulting disiloxane compound with acrolein. The di-α-cyanopentadienoate disiloxane compounds are useful as instant adhesives and as co-monomers in cyanoacrylate or cyanopentadienoate instant adhesives, providing the adhesive polymers or copolymers with improved thermal resistance.

15 Claims, No Drawings

FOREIGN PATENT DOCUMENTS

| | | |
|---|---|---|
| 57-147565 | 9/1982 | Japan . |
| 57-151610 | 9/1982 | Japan . |
| 57-164172 | 10/1982 | Japan . |
| 57-164173 | 10/1982 | Japan . |
| 57-164174 | 10/1982 | Japan . |
| 57-164175 | 10/1982 | Japan . |
| 57-164176 | 10/1982 | Japan . |
| 59-36177 | 2/1984 | Japan . |
| 59-36652 | 2/1984 | Japan . |
| 59-47272 | 3/1984 | Japan . |
| 59-49099 | 3/1984 | Japan . |
| 59-64681 | 4/1984 | Japan . |
| 60-115676 | 6/1985 | Japan . |
| 60-133082 | 7/1985 | Japan . |
| 62-77393 | 9/1985 | Japan . |
| 62-215595 | 3/1986 | Japan . |
| 61-145267 | 7/1986 | Japan . |
| 61-168607 | 7/1986 | Japan . |
| 1-56687 | 8/1987 | Japan . |
| 63-12677 | 1/1988 | Japan . |
| 63-66276 | 3/1988 | Japan . |
| 63-118387 | 5/1988 | Japan . |
| 64-56687 | 3/1989 | Japan . |
| 3-167279 | 7/1991 | Japan . |
| 4-154880 | 5/1992 | Japan . |
| 4-202195 | 7/1992 | Japan . |
| 5-241213 | 9/1993 | Japan . |
| 1374464 | 11/1974 | United Kingdom . |
| 1415102 | 11/1975 | United Kingdom . |
| 405873 | 4/1974 | U.S.S.R. . |
| 446198 | 8/1977 | U.S.S.R. . |
| 438260 | 10/1977 | U.S.S.R. . |
| 744018 | 6/1980 | U.S.S.R. . |

DI-α-CYANOPENTADIENOATE DISILOXANE COMPOUNDS FOR USE IN ADHESIVES

BACKGROUND OF THE INVENTION

Silicon containing α-cyanoacrylate monomers are known.

Buck, U.S. Pat. No. 4,012,402, discloses bis-(alkyl cyanoacrylate) substituted diorganosiloxanes, prepared by a cumbersome Dieis-Alder/reverse Dieis-Alder reaction procedure which is not practical for large quantity commercial synthesis.

Kadykov, et. al., *Plast. massy*, 1984, No. 10, pp 8–9, alleges that diacryl-α-cyano-β-hydroxypropyldimethylsiloxane was synthesized by reaction of cyanoacrylic acid and diepoxydimethylsiloxane in the presence of tertiary amine catalyst.

Diechert, U.S. Pat. No. 4,153,641, states that diorganosiloxane acrylic monomers, including siloxane cyanoacrylic monomers of the general type disclosed in U.S. Pat. No. 4,012,402, may be used in the preparation of acrylic contact lens formulations but does not illustrate synthesis or use of any such siloxane cyanoacrylates.

Monocyanoacrylate ester compounds having silicon substitution are disclosed in Mikuni, et. al., U.S. Pat. No. 5,140,084.

2-Cyano-2,4-pentadienoate esters are well-known monomers that cure by an anionic mechanism and have activity similar to cyanoacrylate esters. The prior art contains references to homopolymerization and polymerization in mixture with cyanoacrylates and other monomers.

Birch, et. al., *J. Chem. Soc.*, 1923, 2448, discloses the reaction of diethyl ketone and ethyl cyanoacetate, catalyzed by zinc chloride.

Gerber, U.S. Pat. No. 3,316,227 (1967); and *Polym. Prepr. Amer. Chem. Soc., Div. Polym. Chem.*, 1968,9(1), 434–41, discloses the reaction of acrolein and ethyl cyanoacetate, catalyzed by zinc chloride in dioxane solvent.

Rao, et. al., *Tetrahedron Lett.*, 1991, 32(41), 5821–5822, discloses the reaction of aromatic aldehydes and ethyl cyanoacetate, catalyzed by zinc chloride.

Trofimov, et. al., GB 1,415,102 (1975), discloses formulations of cyanoacrylates and cyanopentadienoates exhibiting improved thermal stability.

Quinn, et. al., U.S. Pat. No. 3,554,990, discloses synthesis of cyanopentadienoates and formulations with cyanoacrylates exhibiting improved shear strength.

Teramoto, et. al., U.S. Pat. No. 4,313,865, discloses synthesis of cyanopentadienoates and formulations with cyanoacrylates exhibiting improved impact resistance, peel resistance, heat resistance, and water resistance.

Millet, U.S. Pat. No. 4,425,471, discloses synthesis of cyanopentadienoates and formulations of same with cyanoacrylates exhibiting improved impact and peel strengths.

Yeh, U.S. Pat. No. 5,136,065 discloses propargyl esters of 2-cyano-4-aryl-2,4-pentadienoic acids and the hydrosilation thereof with an organohydrogensilane or organohydrogensiloxane to produce organosilanes and organosiloxanes substituted with 2-cyano-5-aryl-2,4-pentadienoate ester groups. However the 5-aryl group interferes with anionic polymerization so these monomers are not suitable as additives to, or substitutes for, cyanoacrylates. Furthermore, hydrosilation of a propargyl cyanopentadienoate which is not substituted in the 5 position is not a suitable synthetic route for cyanopentadienoate esters because of the much greater reactivity of the 5-unsubstituted cyanopentadienoate group.

In copending U.S. patent application Ser. No. 07/769,511, filed Oct. 1, 1991, incorporated herein by reference, there are described monofunctional silane and siloxane cyanoacrylate and cyanopentadienoate compounds.

SUMMARY OF THE INVENTION

The invention in one aspect comprises di-α-cyanopentadienoate disiloxane compounds of the formula:

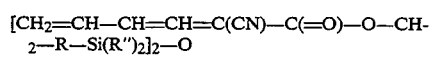

where R is —CH=CH— or —C(=CH$_2$)— and the R" groups are the same or different hydrocarbon or halo substituted hydrocarbon groups.

The di-α-cyanopentadienoate disiloxanes of the invention possess improved thermal stability, as determined by thermal gravimetric analysis (TGA), over non-siloxane-containing α-cyanopentadienoates. Further, the siloxane moiety may be used to impart hydrophobicity and water resistance to polymers or copolymers of the inventive compounds. The difunctionality of the α-cyanopentadienoate compounds results in crosslinked cured products.

The invention further provides a relatively facile synthetic route to difunctional α-cyanopentadienoates. The preferred synthetic route to the compounds of the invention, eliminates alcohol residues that may potentially destabilize subsequent adhesive formulations.

The compounds of the invention are anionically polymerizable and therefore are useful as adhesives alone or in admixture with other α-cyanopentadienoate or α-cyanoacrylate monomer compounds.

DETAILED DESCRIPTION OF THE INVENTION

The inventive compounds are prepared from a bis-cyanoacetoxypropenyldisiloxane compound by condensation of the cyanoacetoxy groups thereof with acrolein. The bis-cyanoacetoxypropenyldisiloxane compounds are preferably obtained by a two step reaction involving (1) hydrosilation of propargyl cyanoacetate with a silicon hydride functional silane:

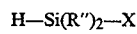

where X is a hydrolyzable group, to produce a hydrolyzable cyanoacetoxypropenylsilane:

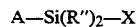

where A is the cyanoacetoxypropenyl group, and then (2) preparing the dicyanoacetoxypropenyldisiloxane:

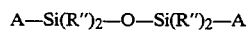

from the hydrolyzable silane by hydrolysis. Alternatively the cyanoacetoxypropenyldisiloxane may be obtained directly by hydrosilation of propargyl cyanoacetate with a silicon hydride functional organosiloxane such as tetramethyldisiloxane.

The hydrolysis method is preferred for its ease in obtaining a disiloxane product, since residues are not formed which could destabilize the final α-cyanopentadienoate. To that end, it is preferred to use in the hydrolysis reaction a mild basic catalyst which can be easily eliminated, particularly an alkali bicarbonate such as sodium bicarbonate.

Suitably the hydrolyzable group on the silane compounds used in hydrolysis method is chloro, acetoxy, alkoxy, or ketoximo, although other known hydrolyzable groups may also be used. Amino or aminoxy groups should be avoided as the cyanopentadienoate compounds subsequently produced must be free of basic contaminants which would initiate polymerization thereof. Most preferably, the hydrolyzable group is chloro.

The hydrocarbon or halo substituted hydrocarbon group R" may be, for instance, an alkyl group, such as methyl or ethyl; an aromatic group, such as phenyl; or a haloalkyl group such as trifluoropropyl or trichloropropyl. Other hydrocarbon or halohydrocarbon groups, however, may be employed without departing from the invention. For most applications the R" groups will be suitably methyl groups or a mixture of methyl and phenyl groups.

By way of illustration of the preparation of the compounds of the invention, 1,3-bis(2-cyano-2,4-pentadienylpropenyl)- 1,1,3,3-tetramethyldisiloxane (BCPP-TMDS) (III) may be prepared by the acid-catalyzed Knovenagel condensation of 1,3-bis(-cyanoacetoxypropenyl)- 1,1,3,3-tetramethyldisiloxane (II) and acrolein, catalyzed by zinc chloride:

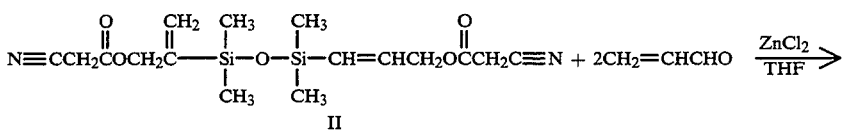

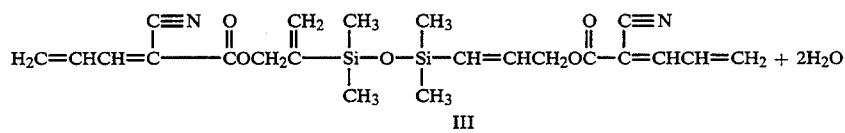

It should be noted that for purposes of this application, compounds II and III respectively, are considered to include the mixed cyanoacetoxypropenyl and cyanopentadienylpropenyl structural isomers, as shown above, as well as their structural isomers in which the respective cyanoacetoxy and cyanopentadienyl end groups are both attached to the linear propenyl group —CH₂—CH=CH— or both are attached to the branched propenyl group —CH₂—C(=CH₂)—.

The starting bis(cyanoacetate) is prepared in two steps. The first step, shown immediately below, is the hydrosilation of propargyl cyanoacetate with chlorodimethylsilane to form cyanoacetoxypropenyl-chlorodimethylsilane (I):

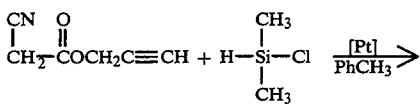

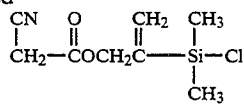

I

Compound (I) also exists as the linear isomer:

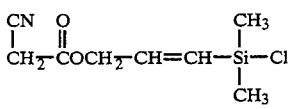

The second step involves hydrolysis of (I) in aqueous sodium bicarbonate to give 1,3-bis(cyanoacetoxypropenyl)-1,1,3.3-tetramethyldisiloxane (II) (shown below as of one of the three isomers believed to be obtained):

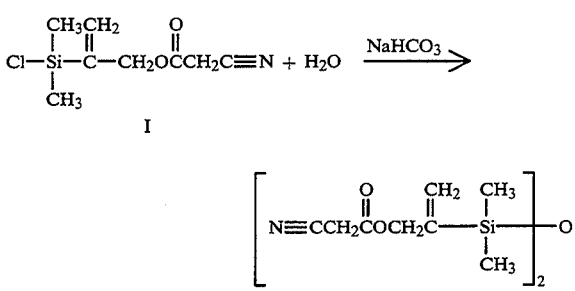

The di-α-cyanopentadienoate disiloxane compounds of the invention are useful as so-called "instant" adhesives, polymerizing spontaneously on contact with very mild bases so that polymerization results from simple contact with most substrates even without special treatment. The adhesive formulations may comprise a single α-cyanopentadienoate monomer of the invention. Alternatively, a mixture of a silicon containing cyanopentadienoate of the invention with another α-cyanopentadienoate monomer and/or a cyanoacrylate monomer can be used. For most applications at least some of the components set forth below will be typically added.

(1) An anionic polymerization inhibitor;
(2) A radical polymerization inhibitor;
(3) A thickener;
(4) Special additives such as cure accelerators, plasticizers tougheners and heat stabilizers;
(5) Perfumes, dyes, pigments, etc.

Suitably the total amount of monomer present in the adhesive composition is about 75 to 99 by weight, based on the total weight of the adhesive composition. The di-α-cyanopentadienoate disiloxane compound of the invention will suitably comprise at least 1%, preferably at least 5% and more preferably at least 25% of the monomer component of the adhesive composition.

An anionic polymerization inhibitor is added to the di-α-cyanopentadienoate disiloxane adhesive composition, e.g., in an amount of about 1 to 1000 ppm based on the total weight of the adhesive composition, to increase the stability of the adhesive composition during storage, and examples of known inhibitors are sulfur dioxide, boron trifluorids, sulfur trioxide, nitric oxide, hydrogen fluoride, and certain sultones. Particularly preferred for purposes of this invention are combinations of methanesulfonic acid (MSA) or hydroxypropanesulfonic acid (HPSA) with sulfur dioxide. Preferred concentrations of sulfonic acids range from about 5 to about 100, more preferably about 10 to 50, parts per million (based on monomer weight). The preferred concentrations of $SO_2$ range from about 15 to about 50 ppm for either acid.

The di-α-cyanopentadienoate disiloxane adhesive compositions of this invention will generally also contain an inhibitor of the radical polymerization. The most desirable of these inhibitors are of the phenolic type, such as quinone, hydroquinone, t-butyl catechol, p-methoxyphenol, etc.

The above inhibitors may be used Within wide ranges, but the following general guidelines are representative of the adhesive composition: acid gases, from about 0.0001% to about 0.06% by weight; suitones, from about 0.1% to about 2% by weight; sulfonic acids, from about 0.0005% to about 0.1% by weight; and free radical inhibitors, from about 0.001% to about 1%.

A thickener may be added to increase the viscosity of the di-α-cyanopentadienoate disiloxane adhesive composition, especially if the di-α-cyanopentadienoate disiloxane compounds of the invention are blended with other monomers of low viscosity. The α-cyanoacrylate monomers, for instance,. generally have a low viscosity of about several centipoise (equivalent to mPa. sec) their unthickened adhesives will readily penetrate into porous materials such as wood and leather or adherents having a rough surface. Thus, good adhesion strengths can be difficult to obtain. Various polymers can be used as thickeners and examples include poly(methyl) methacrylate, methacrylate-type copolymers, acrylic rubbers, cellulose derivatives, polyvinyl acetate and poly-(α-cyanoacrylate). A suitable amount of thickener is generally about 20% by weight or less based on the total weight of the adhesive composition.

A number of conventional polymer additives may also be added for toughening purposes. Examples include acrylic elastomers, acrylonitrile copolymer elastomers and fluoro elastomers. In appropriate amounts such materials may serve as both thickener and toughener.

Certain fumed silica fillers may also be usefully employed as cyanopentadienoate adhesive thickeners. Silicas which are known for use in cyanoacrylate formulations, such as silicas treated with polydialkylsiloxanes as disclosed in U.S. Pat. No. 4,477,607, may be usefully employed.

As examples of cure accelerators there are, for instance, crown ethers, crown ether analogs, and other compounds such as are disclosed in U.S. Pat. No. 4,313,865 at column 4, line 36—column 5, line 52.

The invention is further illustrated by the following non-limiting examples.

EXAMPLE 1

Preparation of cyanoacetoxypropenylchlorodimethylsilane (I)

Chlorodimethylsilane (29.59 g, 0.313 mol) was added dropwise at 80° C. to a solution of 35.0 g (0.284 mol) propargyl cyanoacetate, 0.1 g of a solution of 1,3 divinyl- 1,1,3,3-tetramethyldisiloxane/Pt(0) complex containing 5 wt % platinum in xylenes (Karstedt catalyst) and 50 ml toluene under a nitrogen blanket. The reaction was stirred 3 hours at 80° C. after the addition. An IR spectrum confirmed disappearance of SiH at 2160 $cm^{-1}$. After removing low-boiling volatiles by rotary evaporation, the crude product was purified by vacuum distillation. Upon removal of a small forecut at 80° C. at 0.1 mm Hg, the product distilled at 100°–115° C. at 0.1 m Hg. Yield: 47.1 g (76%) of a clear, greenish tinged liquid. Its structure was confirmed to be cyanoacetoxypropenylchlorodimethylsilane by IR and proton NMR.

EXAMPLE 2

Preparation of 1,3-bis(cyanoacetoxypropenyl)tetramethyldisiloxane (II)

Cyanoacetoxypropenylchlorodimethylsilane (I)(69.23 g, 0.318 mol) was added dropwise to a rapidly stirred solution of 150 ml water and 28.05 g sodium bicarbonate, controlling the foaming by the addition rate. The reaction was stirred 2 hours at 50° C. after the addition. Then, 1 ml concentrated hydrochloric acid was added and the reaction stirred briefly. After extracting with 50 ml toluene, the upper layer was removed and vacuum stripped to remove solvent followed by a deep strip at 70° C. and 0.2 mm/Hg for 2 hours to give 55.2 g (95%) of a reddish oil. Its structure was confirmed to be 1,3-bis(cyanoacetoxypropenyl)tetramethyldisiloxane, including both 2-cyanoacetoxypropenyl groups and 3-cyanoacetoxypropenyl groups, by IR and proton NMR.

EXAMPLE 3

Preparation of 1,3-bis-(2-cyano-2,4-pentadienoylpropenyl)-1,1,3,3-tetramethyldisiloxane (BCPP-TMDS) (III)

Zinc chloride (5.0 g, 0.037 mol) was dissolved in 10.94 g (0.03 mol) (1,3 bis(cyanoacetoxypropenyl)tetramethyldisiloxane (II) and 0.01 g hydroquinone in 25 ml tetrahydrofuran, with a mild exotherm. Upon cooling to room temperature, 5 ml (0.037 mol, 97% purity) acrolein was added and the reaction stirred 1 hour at R. T., followed by heating to 50° C. After 10 hours, IR showed just a trace of unconjugated nitrile absorption at 2280 $cm^{-1}$ compared to the conjugated nitrile absorption at 2230 $cm^{-1}$. After gravity filtering, then adding 0.01 g hydroquinone, solvent was removed by rotary evaporation at 50° C., followed by a deep strip at 50° C. and 0.2 mm/Hg to isolate the product. Yield: 12.4 g (90%) of a viscous red oil. Its structure was confirmed by IR and proton NMR.

The product of this example was subjected to a test cure between glass slides. Fixture was obtained in 2 hours; hard cure in 24 hours.

EXAMPLE 4

Synthesis of neopentyl 2-cyanopenta-2,4-dienoate

To a 1 liter, 3-necked glass reaction flask equipped with a mechanical stirrer, pressure compensating addition funnel and thermometer was added 1,4-dioxane (300 mls), zinc chloride (62.7 g; 0.46 moles), neopentyl cyanoacetate (116.25 g; 0.75 moles) and 1 ml of a solution of 1,4-hydroquinone, prepared by dissolving 1.22 g 1,4-hydroquinone in 100 mls 1,4-dioxane. The mixture was stirred and cooled by means of an ice bath, while a solution of acrolein (52.54 g; 0.94 moles) in 1,4-dioxane (200 mls) was added slowly from the addition funnel. The rate of addition was adjusted such that the reaction temperature did not exceed 40° C. After the reaction exotherm had subsided, the cooling bath was removed and the mixture stirred for a further 5 days. The solvent was removed by distillation under reduced pressure at 28° C. and 45 mbar and the reaction product was transferred to a 2-liter flask. Hexane (900 mls) was added and a yellow polymeric precipitate was formed. The hexane solution was decanted from the polymer and washed 3 times with 1200 ml portions of cold 0.1M hydrochloric acid solution, dried over anhydrous sodium sulfate and the solvent removed by distillation under reduced pressure to yield crude neopentyl 2-cyanopenta-2,4-dienoate (54.95 g; 38%) as a low viscosity orange colored liquid. The structure of the monomer was confirmed by proton NMR and IR analysis. The monomer was stabilized by the addition of 0.6 mg (approximately 10 ppm) of methane sulfonic acid. This monomer was used without further purification in the preparation of the BCPP-TMDS compositions.

EXAMPLE 5

Synthesis of isopropyl 2-cyanopenta-2,4-dienoate

Isopropyl 2-cyanopenta-2,4-dienoate was prepared by a similar process from isopropyl cyanoacetate. In this case the stabilized crude product was vacuum distilled in a Kugelrohr apparatus at 130°–160° C. and 0.6 mm Hg. The monomer was used in the preparation of the BCPP-TMDS compositions without further treatment.

EXAMPLE 6

Adhesive Testing

Instant adhesive compositions containing the inventive monomer BCPP-TMDS were prepared by formulation with isopropyl 2-cyano-2,4-pentadienoate, neopentyl 2-cyano-2,4 pentadienoate, and ethyl cyanoacrylate. The compositions were used to evaluate the effect of BCPP-TMDS on cured properties of mixtures therewith. The following formulations were prepared by admixing at room temperature:

AA: 10% BCPP-TMDS in isopropyl 2-cyano-2,4-pemadienoate
AB: 25% BCPP-TMDS in isopropyl 2-cyano-2,4-pentadienoate
AC: 50% BCPP-TMDS in isopropyl 2-cyano-2,4-pemadienoate
BA: 10% BCPP-TMDS in neopentyl 2-cyano-2,4-pentadienoate
BB: 25% BCPP-TMDS in neopentyl 2-cyano-2,4-pemadienoate
BE: 50% BCPP-TMDS in neopentyl 2-cyano-2,4-pentadienoate
BD: 50% BCPP-TMDS in ethyl cyanoacrylate Fixture time was then determined by pressing one drop of the formulation between glass slides and periodically attempting to pull them gently apart:

| BCPP-TMDS FORMULATIONS FIXTURE TIMES ON GLASS SLIDES NO PRIMER | |
|---|---|
| Formulation | Time (min) |
| AA | 2 |
| AB | 5 |
| AC | 30 |
| BA | 1 |
| BB | 5 |
| BC | 30 |
| BD | 1 |
| Ethyl CA | 1 |

Generally, the fixture times increased with increasing BCPP-TMDS concentration, except for the 50% blend in ethyl cyanoacrylate (BD), which fixtured comparably to ethyl CA.

The formulations were then tested on grit-blasted steel laps per ASTM D-1002, curing one week at room temperature (4 specimens per formulation on the A series, 5 for the B series, ½" overlap). The test results, shown in the following table (where the standard deviation is set forth parentheses), demonstrate that compositions containing the inventive monomer in mixture with other cyanopentadienoate monomers or cyanoacrylate monomers are useful instant adhesives, obtaining high adhesive strengths in the cured compositions.

| Formulation | Stress @ Max. Load - psi | Strain @ Max. Load - % | Stress @ Auto Break - psi | Strain @ Auto Break - % |
|---|---|---|---|---|
| AA | 1395 (67) | 1.754 (0.198) | 1372 (125) | 1.800 (0.259) |
| AB | 1484 (37) | 1.969 (0.231) | 1450 (44) | 2.009 (0.211) |
| AC | 1561 (289) | 1.800 (0.469) | 1489 (359) | 1.920 (0.415) |
| BA | 1796 (138) | 2.449 (0.166) | 1745 (157) | 2.489 (0.103) |
| BB | 1850 (143) | 2.200 (0.141) | 1834 (136) | 2.280 (0.179) |
| BC | 1802 (62) | 2.080 (0.109) | 1790 (68) | 2.080 (0.109) |
| BD | 1516 (773) | 1.7330 (1.091) | 1516 (773) | 1.7330 (1.091) |
| Isopropyl CPD | 1828 (131) | 2.434 (0.154) | 1755 (152) | 2.474 (0.092) |
| Ethyl CA | 3186 (174) | 5.397 (0.465) | 3170 (177) | 5.437 (0.406) |

The neopentyl 2-cyano-2,4-pentadienoate formulations generally outperformed the isopropyl 2-cyano-2,4-pentadienoate blends and were comparable to the neat isopropyl 2-cyano-2,4 pentadienoate. The 50% dimer in ethyl cyanoacrylate blend (BD) tensile data exhibited large scatter, with 2500 psi tensile on two specimens and 900 psi on two others.

EXAMPLE 7

Thermal Gravimetric Analysis (TGA) of difunctional siloxane 2 cyanopentadienoate (BCPP-TMDS)

A 0.5 g sample of BCPP-TMDS was polymerized by stirring the monomer with a small stick onto which the polymerization initiator N,N,N,N-tetramethylethylenediamine had been previously adsorbed. The polymerization reaction was initiated almost instantaneously and completed over a period of several seconds. The polymer was allowed to stand at room temperature for 30 minutes to ensure that the reaction exotherm had completely dissipated prior to analysis. The cured material was rubbery and partially insoluble in acetone, which indicated that some crosslinking had occurred.

For comparative purposes other related polymers were prepared by similar methods. These included polymers of ethyl 2-cyanoacrylate (PECA); 3'-trimethylsilylpropyl 2-cyanoacrylate (TMSPCA); octyl 2-cyanopentadienoate (OCPD); and ethylene glycol bis 2-cyanopentadienoate (EG-CPD), all of which are anionically polymerizable monomers.

Small samples of the various polymers were cut with a clean sharp scalpel blade and the thermal decomposition of the products determined by TGA (DuPont 951 thermogravimetric analyzer). Sample sizes were in the range 5–8 mg. Decomposition mass-loss thermograms was recorded as the % weight change of the original sample over the temperature range from ambient to 600° C. at a heating rate of 10° C./min. Automatic step analyses were conducted on the final thermograms using a coupled TGA computer program (DuPont General Analysis Program) and the temperatures corresponding to the onset of decomposition recorded for each polymer sample.

The onset temperature, determined in this manner, is one of the most important thermal parameters of a polymer from a practical standpoint: it provides information of the maximum service temperature to which the material may be exposed, for short periods, without significant degradation of the material properties. The results that were obtained for the above polymers were as follows:

| POLYMER | ONSET DECOMPOSITION TEMPERATURE (°C.) |
| --- | --- |
| PECA | 171 |
| TMSPCA | 230 |
| OCPD | 240 |
| EG-CPD | 207 |
| BCPP-TMDS | 262 |

The results clearly show that the new monomer BCPP-TMDS has superior thermal resistance properties compared to a conventional cyanoacrylate (PECA), a specialty high temperature cyanoacrylate (TMSPCA), and mono- and di-functional cyanopentadienoate polymers (OCPD and EG-CPD, respectively). The monomers selected for the comparative study are representative components of all the commercially important classes of instant adhesive products known to be in use or under development at present.

What is claimed is:

1. A silicon containing di-α-cyanopentadienoate disiloxane compound of the formula:

$$[CH_2=CH-CH=C(CN)-C(=O)-O-CH_2-R-Si(R'')_2]_2-O$$

where R is —CH=CH— or —C(=CH$_2$)— and the R" groups are the same or different hydrocarbon or halo substituted hydrocarbon groups.

2. The compound according to claim 1 in which the R" groups are independently alkyl, aromatic or haloalkyl groups.

3. The compound according to claim 1 which is 1,3-bis(2-cyano-2,4-pentadienoylpropenyl)-1,1,3,3-tetramethyldisiloxane.

4. The compound according to claim 1 in which the R" groups are a mixture of methyl and phenyl groups.

5. A method of forming a compound as in claim 1 comprising:

hydrolyzing a compound of the formula:

$$A-Si(R'')_2-X$$

where A is a cyanoacetoxypropenyl group, R" is as defined in claim 1 and X is a hydrolyzable group, to produce a compound of the formula:

$$A-Si(R'')_2-O-Si(R'')_2-A$$

and then, condensing the compound A—Si(R")$_2$—O—Si(R")$_2$—A with acrolein.

6. A method as in claim 5 wherein the hydrolysis step is carried out in the presence of an alkali bicarbonate catalyst.

7. A method as in claim 6 wherein the alkali bicarbonate is sodium bicarbonate.

8. A method as in claim 6 wherein said hydrolyzable group is selected from chloro, alkoxy, acetoxy and ketoximo.

9. A method as in claim 6 wherein the compound A—Si(R")$_2$—X is a cyanoacetoxypropenylchlorodialkylsilane.

10. A method as in claim 5 wherein the compound A—Si(R")$_2$—O—Si(R")$_2$—A is 1,3-bis(cyanoacetoxypropenyl)tetramethyldisiloxane.

11. A polymerizable composition comprising a monomer component which includes a silicon containing di-α-cyanopentadienoate disiloxane compound as in claim 1 and an anionic polymerization inhibitor.

12. A composition as in claim 11 wherein the di-α-cyanopentadienoate disiloxane compound comprises at least 5% by weight of the monomer component of the composition.

13. A composition as in claim 11 wherein the di-α-cyanopentadienoate disiloxane compound is 1,3-bis(2-cyano-2,4-pentadienoylpropenyl)-1,1,3,3-tetramethyldisiloxane.

14. A composition as in claim 11 wherein the monomer component further comprises a non-silicon containing α-cyanopentadienoate compound.

15. A composition as in claim 11 wherein the monomer component further comprises an α-cyanoacrylate compound.

* * * * *

UNITED STATES PATENT AND TRADEMARK OFFICE
CERTIFICATE OF CORRECTION

PATENT NO. : 5,386,047
DATED : January 31, 1995
INVENTOR(S) : Nakos et al

It is certified that error appears in the above-indentified patent and that said Letters Patent is hereby corrected as shown below:

Column 5, line 27, delete "Within", insert --within--.

Column 5, line 30, delete "suitones", insert --sultones--.

Column 6, line 13, delete "Sill", insert --SiH--.

Signed and Sealed this

Eighteenth Day of April, 1995

Attest:

BRUCE LEHMAN

Attesting Officer

*Commissioner of Patents and Trademarks*